US008889895B2

(12) United States Patent
Hietsch et al.

(10) Patent No.: US 8,889,895 B2
(45) Date of Patent: Nov. 18, 2014

(54) PROCESS FOR THE DISTILLATION OF FATTY ACID ESTERS

(75) Inventors: Dieter Hietsch, Illertissen (DE); Peter Horlacher, Bellenberg (DE)

(73) Assignee: Cognis IP Management GmbH (DE)

( * ) Notice: Subject to any disclaimer, the term of this patent is extended or adjusted under 35 U.S.C. 154(b) by 0 days.

(21) Appl. No.: 14/000,443

(22) PCT Filed: Mar. 3, 2012

(86) PCT No.: PCT/EP2012/000967
§ 371 (c)(1),
(2), (4) Date: Aug. 20, 2013

(87) PCT Pub. No.: WO2012/119745
PCT Pub. Date: Sep. 13, 2012

(65) Prior Publication Data
US 2013/0331588 A1    Dec. 12, 2013

Related U.S. Application Data

(60) Provisional application No. 61/450,158, filed on Mar. 8, 2011.

(30) Foreign Application Priority Data

Mar. 8, 2011 (EP) .................................. EP11157277

(51) Int. Cl.
    C11C 3/10     (2006.01)
    C07C 69/587   (2006.01)
    C07C 67/54    (2006.01)
    C11C 1/10     (2006.01)
    C07C 67/60    (2006.01)
    C11C 3/00     (2006.01)

(52) U.S. Cl.
    CPC .............. *C07C 67/54* (2013.01); *C07C 69/587* (2013.01); *C11C 1/10* (2013.01); *C07C 67/60* (2013.01); *C11C 3/003* (2013.01)
    USPC .......................................... 554/169; 554/224

(58) Field of Classification Search
    USPC .................................................. 554/16, 224
    See application file for complete search history.

(56) References Cited

U.S. PATENT DOCUMENTS

2012/0308710 A1   12/2012   Beck et al.
2012/0308711 A1   12/2012   Schwaier et al.

FOREIGN PATENT DOCUMENTS

| CA | 2814849 | | 4/2012 | |
|----|---------|---|--------|---|
| EP | 0292846 | A2 | 11/1988 | |
| WO | WO-87/03899 | A1 | 7/1987 | |
| WO | WO 8703899 | A1 * | 7/1987 | ................ C11B 3/00 |
| WO | WO 2004007655 | A1 * | 1/2004 | ................ C11B 3/14 |
| WO | WO-2004007655 | A1 | 1/2004 | |
| WO | WO-2004043894 | A1 | 5/2004 | |
| WO | WO 2004043894 | A1 * | 5/2004 | ............. C07C 67/03 |
| WO | WO-2011095284 | A1 | 8/2011 | |
| WO | WO-2011095305 | A1 | 8/2011 | |
| WO | WO-2011095306 | A1 | 8/2011 | |
| WO | WO-2012048792 | A1 | 4/2012 | |
| WO | WO-2012119745 | A1 | 9/2012 | |

OTHER PUBLICATIONS

U.S. Appl. No. 61/450,158.
U.S. Appl. No. 14/000,443.
U.S. Appl. No. 13/879,040.
Esteban, L., et al., "Synthesis of 2-monoacylglycerols (2-MAG) by enzymatic alcoholysis of fish oils using different reactor types", Biochemical Engineering Journal, vol. 44, (2009), pp. 271-279.
International Search Report for PCT/EP2012/000967 mailed Apr. 25, 2012.
Translation of the International Preliminary Report on Patentability for PCT/EP2012/000967 dated Sep. 10, 2013.

* cited by examiner

*Primary Examiner* — Deborah D Carr
(74) *Attorney, Agent, or Firm* — Drinker Biddle & Reath LLP

(57) ABSTRACT

The present invention relates to a method for working up a mixture which contains esters of EPA and/or DHA with monohydric alcohols having 1 to 6 carbon atoms, esters of other fatty acids with monohydric alcohols having 1 to 6 carbon atoms, and free cholesterol, wherein the method comprises adding a transesterification catalyst to the mixture, converting at least some of the free cholesterol into esterified cholesterol and thereafter distilling the mixture, wherein the distillation is carried out in such a manner that a product is obtained which contains EPA and/or DHA, both in the form of esters thereof with monohydric alcohols having 1 to 6 carbon atoms, in a higher relative amount, based on all fatty acids in free or bound form present in the product, than said mixture. In addition, the present invention relates to a product which is obtainable by the method according to the invention, wherein the product contains 10 to 99.99% by weight of esters of EPA and/or of DHA with monohydric alcohols having 1 to 6 carbon atoms and 0.0001 to a maximum of 0.3 % by weight of cholesterol in free or bound form.

9 Claims, No Drawings

PROCESS FOR THE DISTILLATION OF FATTY ACID ESTERS

CROSS-REFERENCE TO RELATED APPLICATIONS

This application is a national stage application (under 35 U.S.C. §371) of PCT/EP2012/000967, filed Mar. 3, 2012, which claims benefit of European Application No. 11157277, filed Mar. 8, 2011; and U.S. Provisional Application No. 61/450,158, filed Mar. 8, 2011.

The present invention relates to a method for working up a mixture which contains esters of EPA and/or DHA with monohydric alcohols having 1 to 6 carbon atoms, esters of other fatty acids with monohydric alcohols having 1 to 6 carbon atoms, and free cholesterol, wherein the method comprises adding a transesterification catalyst to the mixture, converting at least some of the free cholesterol into esterified cholesterol and thereafter distilling the mixture, wherein the distillation is carried out in such a manner that a product is obtained which contains EPA and/or DHA, both in the form of esters thereof with monohydric alcohols having 1 to 6 carbon atoms, in a higher relative amount, based on all fatty acids in free or bound form present in the product, than said mixture. In addition, the present invention relates to a product which is obtainable by the method according to the invention, wherein the product contains 10 to 99.99% by weight of esters of EPA and/or of DHA with monohydric alcohols having 1 to 6 carbon atoms and 0.0001 to a maximum of 0.3% by weight of cholesterol in free or bound form.

Eicosapentaenoic acid (EPA) and docosahexaenoic acid (DHA) are used in food supplements and in functional foods. EPA and DHA can be obtained, for example, from fish oil, in which both occur in the form of triglycerides.

In order to enrich EPA and DHA from fish oil, the fish oil, which predominantly comprises triglycerides of fatty acids, can be transesterified to give ethyl esters of fatty acids. The ethyl esters of fatty acids may be then separated by distillation. For instance, ethyl esters of EPA and ethyl esters of DHA can be enriched. This is known. It is also known to those skilled in the art how the distillation must be arranged in order to achieve an enrichment of the ethyl esters of EPA and/or DHA compared with the ethyl esters of other fatty acids. For example, a two-stage distillation can be employed, wherein, in a first stage, readily volatile unwanted components are distilled off and the ethyl esters of EPA and/or DHA remain in the distillation bottom phase. In a second stage, then, under a higher vacuum and/or a higher temperature, the ethyl esters of EPA and/or DHA can be distilled off, wherein unwanted components remain in the distillation bottom phase.

Two problems can occur in this case. Firstly, fish oil contains unwanted cholesterol. This occurs partly in free form, partly it occurs as esters with fatty acids, that is to say as cholesterol esters. The free cholesterol has a boiling point which is similar to the boiling points of ethyl ester of EPA and ethyl ester of DHA. Therefore, in the enrichment by distillation of ethyl ester of EPA and ethyl ester of DHA, free cholesterol remains in the desired esters. This is therefore undesirable, inter alia, because cholesterol is frequently considered as undesirable in foods.

WO 2004/007655 discloses a method for reducing the content of free cholesterol in fish oil by entrainment distillation. However, this method does not reduce the content of relatively high-boiling cholesterol esters in fish oil. That is to say, even when the content of free cholesterol in fish oil was reduced, before this is transesterified to ethyl esters from which EPA ethyl esters and DHA ethyl esters can then be enriched by distillation, cholesterol esters remain in the fish oil which must be transesterified. In the transesterification of the fish oil to give ethyl esters, then, free cholesterol is again released from the cholesterol esters, and so in the distillation of the ethyl esters the problem remains that the esters of EPA and DHA that are obtained contain undesirably high amounts of cholesterol.

In addition, the transesterification of the fish oil to give ethyl esters generally does not lead to a complete conversion of the fatty acids from the triglyceride form to the ethyl ester form. Some of the fatty acids remain in the form of monoglycerides bound to glycerol. These monoglycerides are also a problem for the enrichment of the ethyl ester of EPA and ethyl ester of DHA by distillation. Certain fatty acid monoglycerides, e.g. those of hexadecanoic acid, have a boiling point which is similar to the boiling points of the ethyl ester of EPA and ethyl ester of DHA. Therefore, these monoglycerides, in the enrichment by distillation of ethyl ester of EPA and ethyl ester of DHA, remain in the product which contains ethyl ester of EPA and ethyl ester of DHA in an enriched amount. This is also undesirable. Any unwanted monoglycerides present can subsequently be partially removed by crystallizing them out at low temperatures (what is termed winterization).

The problems described in the preceding paragraphs occur not only with the ethyl esters of EPA and DHA, but also in the case of esters thereof with other monohydric alcohols having 1 to 6 carbon atoms, since these have similar boiling points.

Therefore, the object of the present invention is to provide a method which permits a mixture of esters of fatty acids with monohydric alcohols having 1 to 6 carbon atoms which contains free cholesterol and which contains the esters of EPA and/or DHA with monohydric alcohols having 1 to 6 carbon atoms to be worked up in such a manner that the fraction of EPA and/or DHA in the resultant product is increased in comparison to said mixture, wherein the content of free cholesterol in the resultant product shall be lower than in said mixture.

This object is achieved by the method according to the claims of the present invention.

Monohydric alcohols having 1 to 6 carbon atoms are, according to the invention, in particular methanol, ethanol, propanol, n-butanol, n-pentanol and n-hexanol.

A transesterification catalyst is, according to the invention, any catalyst which catalyzes the transesterification of an ester of a carboxylic acid with a first alcohol in the presence of a second alcohol to give an ester of the carboxylic acid with the second alcohol, liberating the first alcohol. In particular, those which may be mentioned here are lipases, alkali metal salts of alkanols, e.g. sodium ethanolate (also termed sodium ethylate).

In addition, the object of the present invention, in a preferred embodiment, is to provide a method in which the content in the resultant product of monoglycerides additionally possibly present in the mixture shall be lower than in said mixture.

This object is achieved by the method according to the invention which is described in its general form in the following, first embodiment.

1. Method for working up a mixture which contains esters of EPA and/or DHA with monohydric alcohols having 1 to 6 carbon atoms, esters of other fatty acids with monohydric alcohols having 1 to 6 carbon atoms and free cholesterol, wherein the method comprises adding a transesterification catalyst to the mixture, converting at least some of the free cholesterol into esterified cholesterol and thereafter distilling the mixture, wherein the distillation is carried out in such a manner that a product is obtained which contains EPA and/or DHA, both in the form of esters thereof with monohydric alcohols having 1 to 6 carbon atoms, in a higher relative amount, based on all fatty acids in free or bound form present in the product, than said mixture.

Preferred embodiments of the method according to the invention are described by the embodiments hereinafter.

2. The method according to embodiment 1, wherein the monohydric alcohols having 1 to 6 carbon atoms are ethanol.

3. The method according to either of the embodiments 1 or 2, wherein the transesterification catalyst is selected from the group consisting of a lipase, an alkali metal salt of a monohydric alcohol having 1 to 6 carbon atoms and sodium ethanolate.

4. The method according to any one of the embodiments 1 to 3, wherein the mixture is obtained from a fish oil, preferably by transesterification with a monohydric alcohol having 1 to 6 carbon atoms (preferably with ethanol).

5. The method according to any one of the embodiments 1 to 4, wherein the mixture contains 10 to 40% by weight esters of EPA and/or DHA with monohydric alcohols having 1 to 6 carbon atoms, 50 to 90% by weight esters of other fatty acids with monohydric alcohols having 1 to 6 carbon atoms and 0.1 to 1% by weight free cholesterol.

6. The method according to any one of the embodiments 1 to 5, wherein a washing step, preferably with water, and optionally thereafter a drying step, preferably by drying in vacuum, proceeds between the conversion of at least some of the free cholesterol into esterified cholesterol and the distillation of the mixture.

7. The method according to any one of the embodiments 1 to 6, wherein the mixture is distilled in two stages, wherein, in a first stage, EPA and/or DHA, both in the form of esters thereof with monohydric alcohols having to 6 carbon atoms, are obtained as bottom-phase product, and wherein, in a second stage, the bottom-phase product is subjected to a distillation, in which EPA and/or DHA, both in the form of esters thereof with monohydric alcohols having 1 to 6 carbon atoms, are obtained as overhead product.

8. The method according to any one of the embodiments 1 to 7, wherein the mixture additionally contains monoglycerides of fatty acids, in particular monoglycerides of fatty acids wherein the fatty acids have 14 to 18, in particular 16, carbon atoms and wherein these monoglycerides are present in the mixture preferably in an amount of 1 to 10% by weight.

In addition, the object of the present invention is to provide a mixture of esters of fatty acids with monohydric alcohols having 1 to 6 carbon atoms, which mixture contains the esters of EPA and/or DHA with monohydric alcohols having 1 to 6 carbon atoms, which, although it contains cholesterol in free or bound form, contains it only in a small amount.

This object is achieved by a product which is obtainable by the method according to any one of claims 1 to 8, wherein the product contains 10 to 99.99% by weight, in particular 20 to 99.9% by weight, in particular 30 to 99% by weight, esters of EPA and/or DHA with monohydric alcohols having 1 to 6 carbon atoms, preferably with ethanol, and 0.0001 to a maximum of 0.3% by weight, in particular 0.001 to a maximum of 0.1% by weight, in particular 0.002 to a maximum of 0.05% by weight, in particular 0.002 to a maximum of 0.02% by weight, cholesterol in free or bound form.

In addition, the object of the present invention, in a preferred embodiment, is to provide a mixture of esters of fatty acids with monohydric alcohols having 1 to 6 carbon atoms, which mixture contains the esters of EPA and/or DHA with monohydric alcohols having 1 to 6 carbon atoms, which, although it contains free cholesterol, only contains it in a small amount, wherein the mixture in addition, although it contains monoglycerides, contains these likewise only in a small amount.

This object is achieved by a product which is obtainable by the method according to any one of claims 1 to 8, wherein the product contains 10 to 99.99% by weight, in particular 20 to 99.9% by weight, in particular 30 to 99% by weight, esters of EPA and/or DHA with monohydric alcohols having 1 to 6 carbon atoms, preferably with ethanol, and 0.0001 to a maximum of 0.3% by weight, in particular 0.001 to a maximum of 0.1% by weight, in particular 0.002 to a maximum of 0.05% by weight, in particular 0.002 to a maximum of 0.01% by weight, cholesterol in free or bound form, wherein this product additionally contains 0.01 to 5% by weight, in particular 0.02 to 4% by weight, in particular 0.03 to 3% by weight, in particular 0.05 to 1% by weight, monoglycerides of fatty acids, in particular monoglycerides of fatty acids wherein the fatty acids have 14 to 18, in particular 16, carbon atoms.

EXAMPLES

Percentages denote percent by weight, unless stated otherwise.

Example 1

Comparative Example

Transesterification 400.0 g of fish oil 20/10 (fish oil with 20% EPA and 10% DHA based on all fatty acids) (total cholesterol content: 0.36% by weight) were placed in a 2 l three-neck flask and inertized with nitrogen. Then, 120.0 g of absolute ethanol and 12.5 g of sodium ethylate (sodium ethoxide) (20% by weight in ethanol) were added, the reaction mixture was heated up and allowed to react for two hours under reflux. The excess ethanol was distilled off, then the reaction mixture was allowed to stand at 75° C. for one hour for phase separation. The bottom phase (glycerol phase) was separated off and the top phase was washed 3 times with 100 g of warm water at 75° C. After the last washing water was separated off, the batch was dried at 90° C. in a vacuum (25 mbar).

Weight: 416.0 g of fish oil ethyl ester (fish oil EE) 20/10, crude (clear, orange-colored).

Composition of the fish oil ethyl ester (in GC area %):

| | |
|---|---|
| monoglyceride | 5.8 |
| diglyceride | 2.8 |
| triglyceride | n.d. |
| ethyl ester | 91.4 |

Concentration of the EPA/DHA EE in the crude fish oil EE 20/10 was performed by distillation in a known manner as described hereinafter.

Distillation 1

416 g of fish oil EE 20/10 crude were distilled by means of a laboratory short path distillation under the following conditions:

Oil temperature 95° C./pressure 0.02 mbar/feed 3.8 g per min/degasser 75° C./internal cooler 40° C.

Distillate: 245.4 g (virtually colorless, clear, 59%)

Residue: 170.6 g (orange, clear, 41%)

Distillation 2

The residue from distillation 1 was again distilled by means of short path distillation:

Oil temperature 180° C./pressure 0.015 mbar/feed 2.7 g per min/degasser 75° C./internal cooler 40° C.

Residue: 13.7 g (reddish-orange, virtually clear, 8%)
Distillate: 156.9 g (light-yellow, clear, 92%)

Separation of Insolubles

For separating off the components insoluble at 0° C., the ethyl ester concentrate (distillate of distillation 2) was stored overnight at 0° C. and filtered on the next morning by means of a laboratory vacuum filter which was equipped with the Beco CP1 KS 4L filter plate.

Filtrate: 140.0 g
Filter cake: 16.9 g (10.8%)
Composition of the filtrate:

| | |
|---|---|
| Monoglyceride (GC area %) | 10.0 |
| Ethyl ester (GC area %) | 90.0 |
| Cholesterol (% by weight) | 0.34 |

As shown in the table, the total cholesterol content virtually corresponded to the initial value of 0.36% by weight.

Example 2

According To the Invention

Transesterification 400.0 g of fish oil 20/10 (total cholesterol content: 0.36% by weight) were placed in a 2 l three-neck flask and inertized with nitrogen. Then, 120.0 g of absolute ethanol and 12.5 g of Na ethylate (20% strength) were added, the reaction mixture was heated up and allowed to react for two hours under reflux. The excess ethanol was distilled off and then the mixture was allowed to stand for one hour at 75° C. for phase separation. The bottom phase (glycerol phase) was separated off. To the residue were added 2.5 g of Na ethylate (20% strength). Then, a vacuum (25 mbar) was applied and the batch was stirred for 2 hours at 110° C. Then, the batch was cooled to approximately 80° C. and atmospheric pressure was established by means of nitrogen. Thereupon, the batch, as described in Example 1, was washed 3 times with water and worked up.

Weight: 410.6 g of fish oil EE 20/10, crude (clear, orange-colored).

Composition of the fish oil ethyl ester (in GC area %):

| | |
|---|---|
| monoglyceride | 2.9 |
| diglyceride | 2.2 |
| triglyceride | 14.3 |
| ethyl ester | 80.6 |

The EPA/DHA EE were concentrated in the crude fish oil EE 20/10 in a similar manner to that described in Example 1. For separating off components insoluble at 0° C., the product (147.8 g) was stored overnight at 0° C. Since no precipitate had formed, filtration was dispensed with, and therefore no filter cake was produced either.

Product composition:

| | |
|---|---|
| Monoglyceride (GC area %) | 4.8 |
| Ethyl ester (GC area %) | 95.2 |
| Cholesterol (% by weight) | <0.01 |

As the table shows, on addition of catalyst (sodium ethylate) to the postreaction, the total cholesterol content was reduced by more than 95%.

Example 3

According To the Invention 450 g of fish oil EE 20/10 (5.7% monoglyceride, 2.2% diglyceride, 0.2% by weight total cholesterol) were placed in a 1 liter three-neck flask and inertized with nitrogen. To this were added 9.0 g of Novozym® 435 NG (an immobilized enzyme of a lipase). The batch was heated to 77° C. and a vacuum of 1 mbar was applied. After 48 hours of reaction time, the mixture was cooled and the immobilized enzyme filtered off.

Weight: 421 g

The EPA/DHA EE were concentrated in the crude fish oil EE 20/10 in a similar manner to that described in Example 1. For separating off components insoluble at 0° C., the product (121.8 g) was stored overnight at 0° C. Since no precipitate had formed, filtration was dispensed with, and therefore no filter cake was produced either.

Product composition:

| | |
|---|---|
| Monoglyceride (GC area %) | 0.1 |
| Ethyl ester (GC area %) | 99.9 |
| Cholesterol (% by weight) | 0.01 |

The invention claimed is:

1. A method for working up a mixture which comprises
    esters of EPA and/or DHA with monohydric alcohols having 1 to 6 carbon atoms,
    esters of other fatty acids with monohydric alcohols having 1 to 6 carbon atoms and
    free cholesterol,
wherein the method comprises
    adding a transesterification catalyst to the mixture,
    converting at least some of the free cholesterol into esterified cholesterol and thereafter
    distilling the mixture,
wherein the distillation is carried out in such a manner that a product is obtained which contains EPA and/or DHA, both in the form of esters thereof with monohydric alcohols having 1 to 6 carbon atoms, in a higher relative amount, based on all fatty acids in free or bound form present in the product, than said mixture.

2. The method according to claim 1, wherein the transesterification catalyst is selected from the group consisting of a lipase, an alkali metal salt of a monohydric alcohol having 1 to 6 carbon atoms and sodium ethanolate.

3. The method according to claim 1, wherein the mixture is obtained from a fish oil by transesterification with a monohydric alcohol having 1 to 6 carbon atoms.

4. The method according to claim 3, wherein the monohydric alcohol is ethanol.

5. The method according to claim 1, wherein the mixture comprises
    10 to 40% by weight esters of EPA and/or DHA with monohydric alcohols having 1 to 6 carbon atoms,
    50 to 90% by weight esters of other fatty acids with monohydric alcohols having 1 to 6 carbon atoms and
    0.1 to 1% by weight free cholesterol.

6. The method according to claim 1, wherein a washing step with water and thereafter a drying step by drying in vacuum proceeds between the conversion of at least some of the free cholesterol into esterified cholesterol and the distillation of the mixture.

7. The method according to claim 1, wherein the mixture is distilled in two stages, wherein, in a first stage, EPA and/or DHA, both in the form of esters thereof with monohydric alcohols having 1 to 6 carbon atoms, are obtained as bottom-phase product, and wherein, in a second stage, the bottom-phase product is subjected to a distillation, in which EPA and/or DHA, both in the form of esters thereof with monohydric alcohols having 1 to 6 carbon atoms, are obtained as overhead product.

8. The method according to claim 1, wherein the mixture further comprises
monoglycerides of fatty acids.

9. A product which is obtained by the method according to claim 1, wherein the product contains
30 to 99.9% by weight esters of EPA and/or DHA with monohydric alcohols having 1 to 6 carbon atoms, preferably with ethanol, and
0.0001 to a maximum of 0.3% by weight cholesterol in free or bound form; wherein the product further comprises 0.01 to 5% by weight monoglycejrides of fatty acids, preferably of fatty acids having 16 carbon atoms.

\* \* \* \* \*